April 11, 1972 D. L. ARMSTRONG Plant Pat. 3,102
ROSE PLANT
Filed Jan. 22, 1970
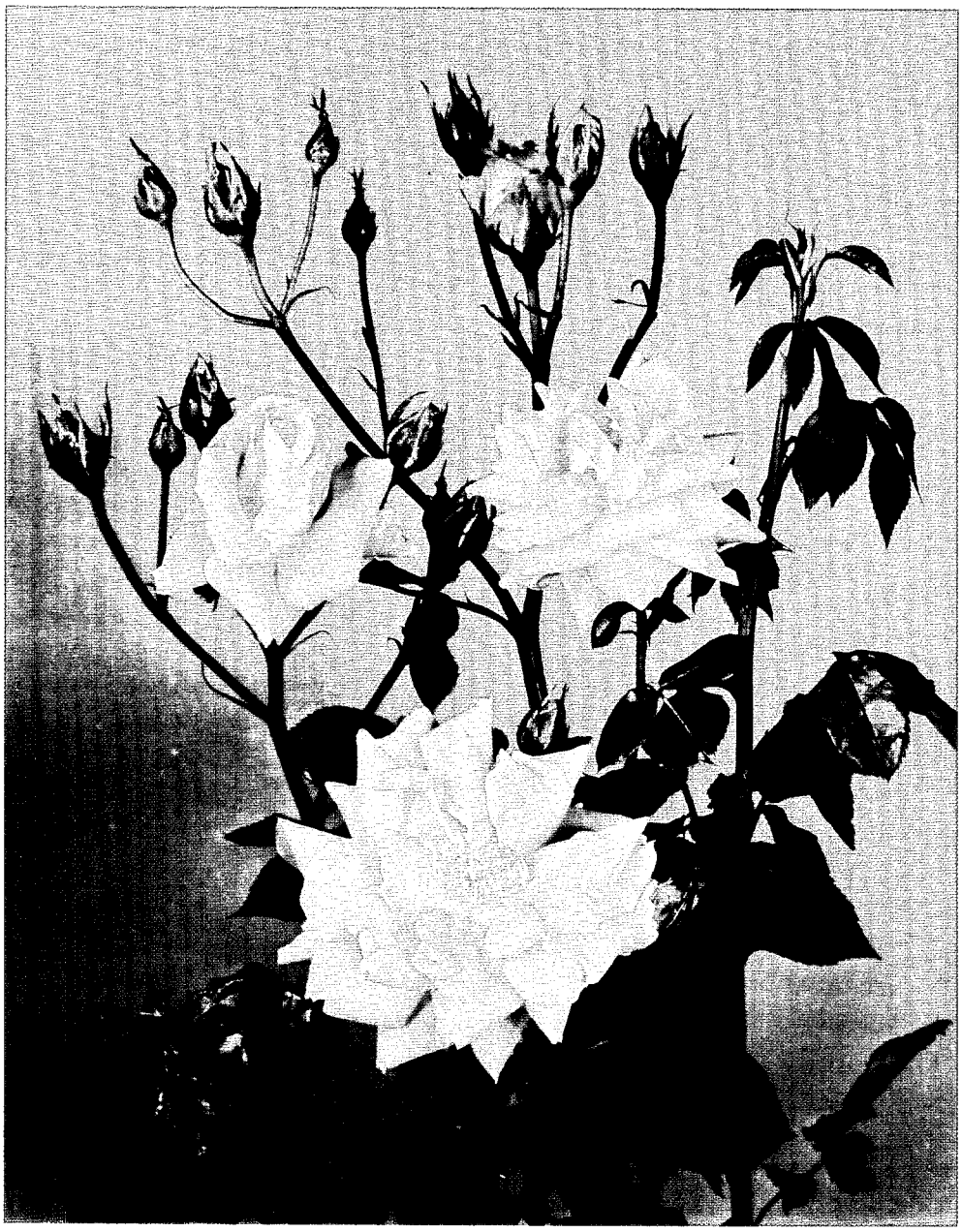

United States Patent Office

Plant Pat. 3,102
Patented Apr. 11, 1972

3,102
ROSE PLANT
David L. Armstrong, Upland, Calif., assignor to Armstrong Nurseries, Inc., Ontario, Calif.
Filed Jan. 22, 1970, Ser. No. 5,163
Int. Cl. A01h 5/00
U.S. Cl. Plt.—25 1 Claim

ABSTRACT OF THE DISCLOSURE

A bushy rose of the floribunda class, tall-growing, moderately branched and moderately vigorous in habit. The plant has compound leaves comprising from three to seven leaflets which are of medium size, moderately thin, somewhat leathery in texture, and semi-glossy in appearance. These leaflets are oval in form, both the apex and the base being acute. The margin is simply serrate. The color of the open bloom is a distinctive strong reddish orange, tinged with yellow on the underside of the petals. When fully open, the center of the bloom shows brilliant golden yellow around the flower stamens. The petalage is double, ranging from twenty-five to thirty petals, with three to eight petaloids. The flower is high-centered in form at the first, and remains high-centered after opening fully. The bloom has a tea fragrance, from moderate to penetrating in strength. The plant sets hips freely, containing many seeds.

This invention relates to a new variety of floribunda bush rose, tall and well adapted for outdoor cultivation and garden decoration.

The seed parent of this new variety is known as "Spartan." The pollen parent was a cross of "Goldilocks," with an unnamed variety produced by crossing "Fandango" and "Pinocchio." The plant holds its distinguishing characteristics through succeeding propagations by budding. It was originally propagated in Ontario, Calif.

Some of the ways in which this new variety differs from its seed parent, "Spartan," are these: "Spartan" manifests a very vigorous, tall growth, whereas the new variety is more branched and bushy: and is only moderately free growing, and comparatively less vigorous in its growth habit. The foliage of "Spartan" has a very characteristic drooping appearance, whereas the foliage of this new variety is carried at an attitude slightly above the horizontal, so as to give a more spritely appearance. The foliage of this new variety is of medium size, as compared to that of the "Spartan" rose, which is considerably larger. The leaves of the new variety are leathery in texture and semi-glossy in appearance. The flowers of the "Spartan" rose are described as very fragrant, whereas the flowers of the new variety have but a moderate fragrance. The color of the "Spartan" flower would be commonly referred to as reddish orange, whereas the flower of the new variety is much more orange, with a definitely yellow cast on the reverse side of the petals.

This new variety is distinguished from its unnamed pollen parent most notably in the following respects: Whereas this new variety is moderately free and vigorous in growth, the pollen parent was moderately weak. The pollen parent only occasionally would produce a seed hip out of doors, while this new variety, when grown under comparable conditions, will produce many hips. The leaves of the pollen parent are quite soft, whereas the leaves of the new variety are somewhat leathery and somewhat moderately thin. The color of the pollen parent is a medium yellow, whereas the new seedling is a yellow and orange bicolor. The new variety blooms nearly continuously during the growing season, whereas the pollen parent bloomed intermittently during the season.

The accompanying drawing illustrates the plant in color, and shows the flowering thereof from bud to full bloom. In the description which follows, the color values stated are based on the Nickerson Color Fan, except where the popular color designation is sufficiently descriptive for present purposes.

The flowers of this new variety are borne sometimes singly, but usually several to a stem in irregular clusters on normal short to medium stems. The plant blooms freely outdoors and nearly continuously during the growing season. The blooms have a moderate to penetrating tea fragrance.

As to the bud: The peduncle is of average length and of slender to average caliper. It is erect, usually smooth, and has some gland-tipped cilia. Its color is Moderate Olive, 7.5Y 4/3, overlaid with dark tones of Dark Red, 2.5R 3/7. Before the calyx breaks, the buds are of small size, moderately short and pointed in form, with foliaceous appendages, a few gland-tipped cilia, and glandular bloom on the surface of the bud, usually with slender foliaceous parts extending beyond the tip of the bud for a distance equal to about one-fourth or more of its length.

As the calyx breaks, the color presents shadings of Strong Red, 5R 4/12, and Dark Red, 5R 3/7, and some spotting of Moderate Yellow Green, 2.5GY 5/5. The inner surface of the sepals carries a fine wooly tomentum. Margins of alternate sepals are lined with stipitate glands and occasional slender foliaceous appendages. The margins of the other sepals are lined with stipitate glands and fine wooly tomentum.

As the first petal opens, it is small in size, short and ovoid in form. The outside of the petal displays a Brilliant Yellow, 5Y 9/9, in a small area at the base, which blends upwards through Moderate Orange Yellow, 10YR 8/10, to nearly Deep Yellowish Pink, 5R 6/11, at the apex. The inside of the petal shows a moderate area at the base which is Vivid Yellow, 5Y 8/12, ending abruptly at a portion colored nearly Strong Reddish Orange, 7.5R 5/13, with some Strong Reddish Orange, 7.5R 6/12, between the veins at the petal apex. The bud opens well and is not retarded or prevented from opening by cold, hot, wet or dry weather.

*Bloom*

When fully open the bloom measures from 3½" to 4". The petalage is double, from 25–30 petals, plus 3–8 petaloids regularly arranged. It is high-centered in form, both at first and upon opening out. The petals at first are somewhat flat, with tips reflexed outward. Later, at maturity, they become somewhat more loosely flat, with tips reflexed outward. The petals are medium thick, slightly satiny on the inside, and shiny to satiny on the outside. The outer petals are broadly obovate, scalloped, but the apex is more rounded, although still having one or two notches. The inside petals are narrowly obovate, also being scalloped, with rounded apex and one or two notches.

The description which follows relates to the flower of a rose grown outdoors, newly opened in the month of April, in Ontario, Calif.

The color of the outside petal, on its outer surface, displayed a nearly Brilliant Yellow, 5Y 9/9, color in a moderate area at the base, with slight streaking of this color on the lower veins, blending into Moderate Orange Yellow, 7.5YR 8/8, and into nearly Strong Yellowish Pink, 5R 7/9. The inner surface of the outside petal displayed a moderate area at the base which was likewise nearly Brilliant Yellow, 5Y 9/9, which which yielded abruptly to a color between Strong Reddish Orange, 7.5R 6/12, and Strong Reddish Orange, 7.5R 5/13. The apex of the petal was nearly Strong Reddish Orange, 7.5R 6/12.

The outer surface of the intermediate petal was nearly Brilliant Yellow, 5Y 9/9, on a small area at the base, blending with Light Orange, 5YR 8/7, through the center of the petal and into nearly Strong Yellowish Pink, 5R 7/9, at the apex. The inner surface of the intermediate petal likewise had a small area at the base which was Brilliant Yellow, 5Y 9/9, yielding abruptly to a color between Strong Reddish Orange, 7.5R 6/12, and Strong Reddish Orange, 7.5R 5/13, for the remainder of the petal.

The outer surface of the inner petal again displayed a small area at the base which was nearly Brilliant Yellow, 5Y 9/9, blending and shading upwards through Light Orange, 5YR 8/7, and into nearly Strong Yellowish Pink, 7.5R 7/9, at the apex. The inner surface of the inner petal had a moderate area at the base which was nearly Brilliant Greenish Yellow, 7.5Y 9/8, yielding abruptly to a color nearly Strong Reddish Orange, 7.5R 6/12, for the remainder of the petal.

The description which follows relates to the bloom of a rose plant grown outdoors in Ontario, Calif., after the flower had been open for three days in the month of April.

The outer surface of the outside petal showed a small area at the base which was Brilliant Yellow, 5Y 9/9, blending gradually with Moderate Orange Yellow, 7.5YR 8/8, and into Strong Pink, 2.5R 7/8. The inner surface of the outer petal showed a moderate area at the base which was nearly Vivid Yellow, 5Y 8/12, yielding abruptly to a color blending between Strong Yellowish Pink, 7.5R 7/9, and Strong Reddish Orange, 7.5R 6/12.

The outer surface of the inside petal showed a small area at the base and midrib partway up the petal colored a Brilliant Yellow, 5Y 9/9, shading to nearly Pale Orange Yellow, 7.5YR 9/4, and then into nearly Deep Pink, 2.5R 6/11, at the apex. The inner surface of the inside petal showed a moderate area at the base which was between Brilliant Greenish Yellow, 7.5Y 9/8, and Vivid Greenish Yellow, 7.5Y 8/12, the remainder being between Strong Yellowish Pink, 7.5R 7/9, and Strong Reddish Orange, 7.5R 6/12.

The general color effect of the newly opened flower lies somewhere between Strong Reddish Orange, 10R 6/12, and Strong Reddish Orange, 7.5R 5/13. After the bloom had been three days open, the general color effect was between Strong Reddish Orange, 7.5R 6/12, and Deep Yellowish Pink, 5R 6/11. The petals drop off cleanly, except for the petaloids and the blooms are not affected by cold, hot, wet, or dry weather.

On the bush in the garden the flowers will persist for four to five days in the month of September in Ontario, Calif. Cut roses grown outdoors and kept at living room temperatures will last from five to six days at the same time and place.

*Reproductive organs*

There are many stamens, arranged regularly about the pistils.

The filaments are short to medium-length, generally from 2 to 10 mm.

The anthers are small to medium size, and all open approximately at the same time. On the upper side they are near Moderate Orange Yellow, 10YR 8/10, in color, and on the underside near Dark Orange Yellow, 10YR 6/8.

The pollen is moderate in amount and near Strong Orange Yellow, 10YR 7/10, in color.

The pistils are few to average in number, there usually being about forty of them.

The styles are moderately even, short to average length, thin, and somewhat tightly bunched. They are 4 to 7 mm. in length. Their color is near Vivid Yellow, 2.5Y 8/12, overlaid with Strong Reddish Orange, 7.5R 5/13, when first open.

The stigma is nearly Moderate Red, 2.5R 4/10, in color.

All of the ovaries are usually enclosed in the calyx.

The hips are average length and globular in form, near Moderate Yellow Green, 2.5GY 5/5, when the hip is at mature size, but not yet ripe. They are smooth with thick, fleshy walls.

The sepals fall soon. They are moderately short, spear-shaped and slightly curled.

The seeds are numerous, usually small to medium size, and varying in number from 25 to 40.

*Foliage*

The foliage is compound, usually with three to seven leaflets. They are of normal medium size, moderately thin, somewhat leathery in texture and semi-glossy in appearance. The leaflets are oval in shape, with apex acute and with the base also acute. The margins are simply serrate. The color of the mature leaf on its upper surface is near Grayish Olive Green, 5GY 3/2, while the under surface is between Moderate Yellow Green, 5GY, 5/6, and Moderate Olive Green, 5GY 4/3. On the young leaves, the color of the upper surface is Dark Greenish Yellow, 7.5Y 6/7, overlaid with near Moderate Reddish Brown, 7.5R 3/6. The under surface of the young leaves is Light Olive, 7.5Y 5/5, overlaid with near Dark Red, 2.5R 3/7.

The rachis is of average size, having its upper side grooved with some stipitate glands on the edges. The underside is smooth. The stipules are of medium length, narrow, with medium-length points turning out at an angle of more than 90°.

The plant has average resistance to mildew, and black spot, in comparison with other varieties now in commerce, when grown under comparable conditions in Ontario, Calif.

*Growth*

The plant is of bushy, moderately branched habit, free and vigorous in growth. The canes are of medium caliper. The main stems are near Moderate Yellow Green, 2.5GY 5/5, in color, and carry a few large prickles which are of medium length, hooked slightly downward, with moderately short narrow bases. Their color is between Strong Yellowish Brown, 7.5YR 5/7, and Moderate Brown, 7.5 YR 4/5. There are no small prickles, nor are there any hairs.

The branches are of near Moderate Yellow Green, 2.5GY 5/5, color. They carry a few large prickles of medium length which are almost straight, but hooked slightly downward, with short narrow bases. Their color is near Light Olive, 5Y 5/6, overlaid with near Dark Red, 5R 3/7. There are a very few small prickles of a color which is near Light Oliver, 5Y 5/6, overlaid with near Moderate Red, 2.5R 4/10. There are no hairs.

The color of the new shoots is near Moderate Yellow Green, 2.5GY 5/5, overlaid with near Dark Red, 5R 3/7, where exposed to the direct sunlight. There are a few large prickles of medium length which are almost straight, with medium-length narrow bases, and having a color which is near Dark Red, 2.5R 3/7. There are very few small prickles, and their color is near Dark Red, 2.5R 3/7. There are no hairs.

I claim:

1. A floribunda bush rose substantially as shown and described herein, and distinguished by novel combinations of features, including: a moderately branched and moderately vigorous habit of growth; compound leaves comprising from three to seven leaflets of medium size, somewhat thin and leathery in texture, semi-glossy in appearance, and generally oval in form but with acute apex and base, and simply serrated margin; a small, short bud which, upon opening, yields a high-centered bloom of a distinctive strong reddish orange color tinged with yellow on the underside of the petals, the center of the bloom, when fully open, displaying brilliant golden yellow around the flower stamens, while retaining its high-centered form, said bloom having a tea fragrance of from moderate to penetrating strength; the plant being further characterized in its tendency to set hips freely, containing many seeds.

No references cited.

ROBERT E. BAGWILL, Primary Examiner